(12) United States Patent
Weiss et al.

(10) Patent No.: US 9,173,341 B2
(45) Date of Patent: Nov. 3, 2015

(54) POSITIONING EQUIPMENT

(71) Applicant: Dow AgroSciences LLC, Indianapolis, IN (US)

(72) Inventors: Anthony Weiss, Lubbock, TX (US); John Mirusso, Delray Beach, FL (US); John D. Busacca, Noblesville, IN (US); Phillip J. Howard, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 23 days.

(21) Appl. No.: 13/950,445

(22) Filed: Jul. 25, 2013

(65) Prior Publication Data

US 2014/0158032 A1    Jun. 12, 2014

Related U.S. Application Data

(60) Provisional application No. 61/734,486, filed on Dec. 7, 2012.

(51) Int. Cl.
| | | |
|---|---|---|
| *A01C 21/00* | (2006.01) | |
| *A01C 7/04* | (2006.01) | |
| *A01C 19/02* | (2006.01) | |
| *A01N 25/26* | (2006.01) | |
| *A01N 25/10* | (2006.01) | |
| *A01N 29/02* | (2006.01) | |
| *A01C 7/20* | (2006.01) | |
| *A01C 15/00* | (2006.01) | |
| *A01N 25/00* | (2006.01) | |

(52) U.S. Cl.
CPC ............... *A01C 21/002* (2013.01); *A01C 7/04* (2013.01); *A01C 7/046* (2013.01); *A01C 7/20* (2013.01); *A01C 15/00* (2013.01); *A01C 19/02* (2013.01); *A01N 25/00* (2013.01); *A01N 25/26* (2013.01)

(58) Field of Classification Search
CPC .......... A01C 7/046; A01C 7/20; A01C 15/00; A01C 21/002; A01C 21/00; A01C 7/04; A01C 7/00; A01C 19/02; A01C 19/00; A01N 25/00; A01N 25/26
USPC .................. 111/15, 170, 174, 177, 183–185; 239/650, 661; 221/200, 202–204, 211
See application file for complete search history.

(56) References Cited

U.S. PATENT DOCUMENTS

| | | |
|---|---|---|
| 3,640,234 A | 2/1972 | Carroll et al. |
| 4,915,258 A | 4/1990 | Olson |
| 6,109,193 A | 8/2000 | Crabb et al. |
| 2005/0120928 A1 | 6/2005 | Horn |
| 2008/0295751 A1 | 12/2008 | Shoup et al. |
| 2011/0098851 A1 | 4/2011 | Glendenning et al. |

OTHER PUBLICATIONS

International Search Report dated Jan. 29, 2014 from application No. PCT/US2013/051957.

*Primary Examiner* — Christopher J Novosad
(74) *Attorney, Agent, or Firm* — Carl D. Corvin; Maschoff Brennan (57) ABSTRACT

Equipment for the placement or positioning of one or more items in or on the ground is provided. In one form, an apparatus includes a toolbar, a container, a metering unit configured to selectively control release of one or more items from the container and an application member configured to deliver the one or more items released from the container to the ground. In one aspect of this form, the metering unit is configured to selectively control release of one or more spherical items having a diameter in the range of about 0.25 inches to about 1.0 inches, and more particularly, but not exclusively, in the range of about 0.5 inches to about 0.75 inches, from the container to the application member. In another more particular aspect, the spherical items are capsules that include a shell wall encapsulating a pesticide composition and including a gelatin material.

36 Claims, 8 Drawing Sheets

POSITIONING EQUIPMENT

CROSS-REFERENCE TO RELATED APPLICATIONS

The present application claims priority to U.S. Provisional Patent Application No. 61/734,486 filed Dec. 7, 2012, the content of which is incorporated herein by reference in its entirety.

BACKGROUND

The present application relates to the placement or positioning of one or more items in or on the ground, and more particularly but not exclusively, to an apparatus configured to position or place one or more spherical capsules in or on the ground, and to techniques for using such an apparatus.

Advances in certain areas of technology have given rise to the need for new approaches for the placement or positioning of certain items relative to the ground. For example, and without limitation, delivery vehicles such as capsules which are configured to degrade after their implantation may be used to deliver a desired composition to a field, grove, orchard or other plant growing environment or locus that is in need of treatment by the desired composition. These capsules may release, amongst other possibilities, pesticide compositions, fertilizer compositions and combinations of the foregoing, and may include a structure that is susceptible to breakage or disruption during handling and under current placement techniques which can result in premature release of the composition therefrom. Beyond rendering the capsules unsuitable for their intended function, the premature release of the composition from the capsules may also undesirably expose the handlers thereof to the compositions being released. Similarly, in certain instances it is desired to minimize direct human handling of such capsules. Accordingly, there is a demand for further improvements in this area of technology.

SUMMARY

Equipment for the placement or positioning of one or more items in or on the ground is provided. In one form, an apparatus includes a toolbar, a container, a metering unit configured to selectively control release of one or more items from the container and an application member configured to deliver the one or more items released from the container to the ground. In one aspect of this form, the metering unit is configured to selectively control release of one or more spherical items having a diameter in the range of about 0.25 inches to about 1.0 inches, and more particularly, but not exclusively, in the range of about 0.5 inches to about 0.75 inches, from the container to the application member. In another more particular aspect, the spherical items are capsules that include a shell wall encapsulating a pesticide composition and including a gelatin material.

In one embodiment, an apparatus includes a toolbar, a container, a metering unit configured to selectively control release of one or more items from the container, an application member configured to deliver the one or more items released from the container to soil, and an actuation system configured to selectively move the container relative to the toolbar.

In another embodiment, an apparatus includes a toolbar, a container, and a metering unit configured to selectively control release of one or more spherical items having a diameter in the range of about 0.5 inches to about 0.75 inches from the container. The metering unit includes a mounting member coupled to the container, a metering cup, and a guide plate positioned between the mounting member and the metering cup. The guide plate includes a central aperture and a thickness dimensioned to facilitate passage of the one or more spherical items from the container through the central aperture to the metering cup for release from the metering unit. The apparatus also includes an application member configured to deliver the one or more spherical items released from the container to soil.

In yet another embodiment, an apparatus includes a toolbar, a container, a vacuum source, and a vacuum metering unit configured to selectively control release of one or more spherical items having a diameter in the range of about 0.5 inches to about 0.75 inches from the container. The vacuum metering unit is coupled with the vacuum source and includes a metering plate having a first side, an opposite second side, and a plurality of substantially spherical indentations on the first side. The indentations are configured to receive and hold a spherical item having a diameter in the range of about 0.5 inches to about 0.75 inches when a vacuum force is applied to the second side by the vacuum source.

In still another embodiment, a method includes positioning a number of capsules in a container of a positioning apparatus. Each of the capsules includes a shell wall encapsulating a pesticide composition and including a gelatin material, and the positioning apparatus includes a toolbar, a metering unit coupled to the container and configured to selectively control release of the capsules from the container, and an application member coupled with the metering unit and configured to deliver the capsules released from the container to soil. The method further includes operating the apparatus relative to adjacent soil to individually position a plurality of the capsules at separate locations in the soil.

Other aspects include unique methods, systems, devices, kits, assemblies, equipment, and/or apparatus related to the placement or positioning of one or more items in or on the ground.

Further aspects, embodiments, forms, features, benefits, objects, and advantages shall become apparent from the detailed description and figures provided herewith.

DETAILED DESCRIPTION OF REPRESENTATIVE EMBODIMENTS

For purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Equipment for the placement or positioning of one or more items in or on the ground is provided. In one form, an apparatus includes a toolbar, a container, a metering unit configured to selectively control release of one or more items from the container and an application member configured to deliver the one or more items released from the container to the ground. In one aspect of this form, the metering unit is configured to selectively control release of one or more spherical items having a diameter in the range of about 0.25 inches to about 1.0 inches, and more particularly, but not exclusively, in the range of about 0.5 inches to about 0.75 inches, from the container to the application member. In another more particular form, the spherical items are capsules that include a shell wall encapsulating a pesticide composition and including a gelatin material.

Figure 1:
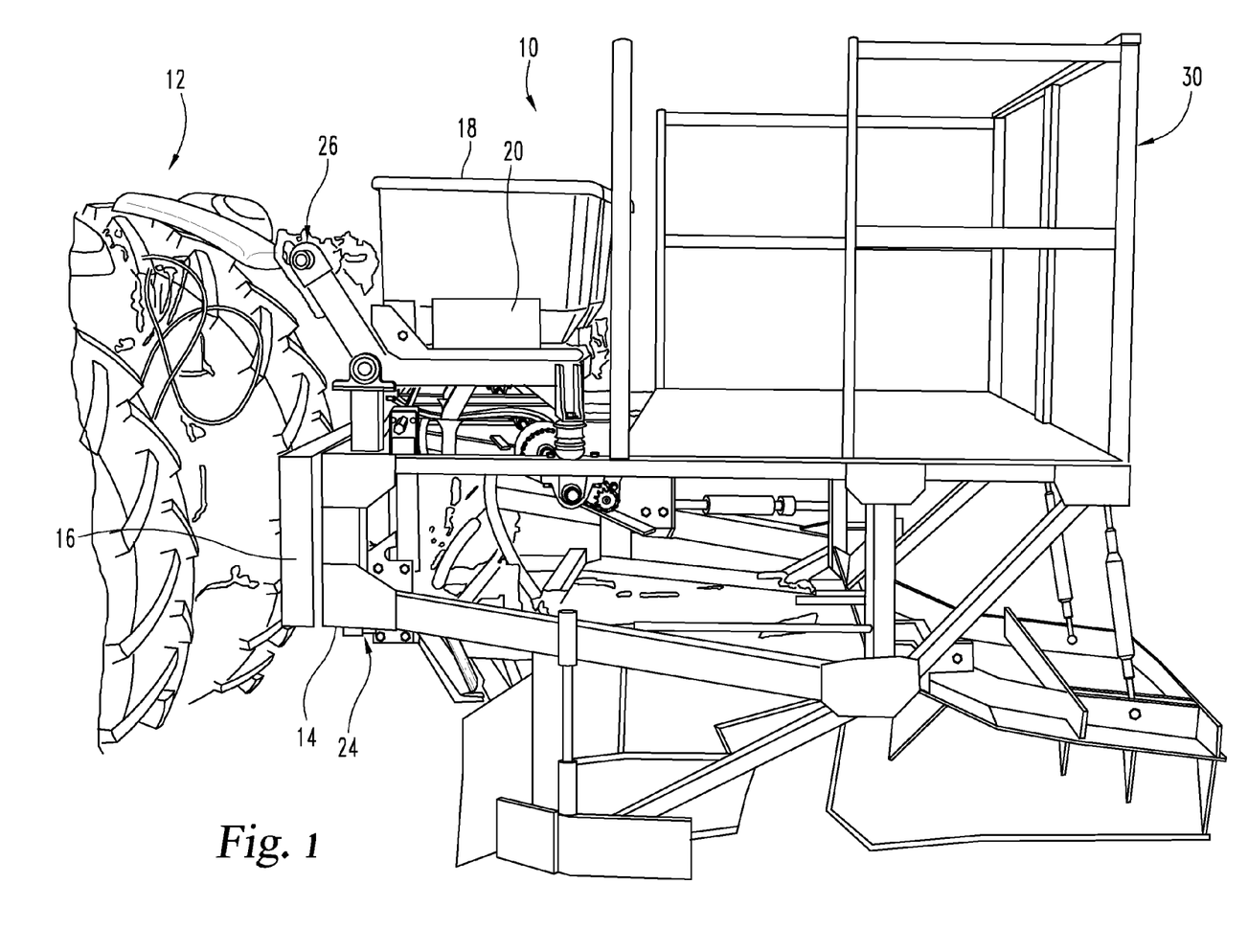
FIG. 1 is a perspective view of a positioning apparatus coupled with an agricultural vehicle.

Turning now to FIG. 1, there is illustrated a positioning apparatus 10 coupled to an agricultural vehicle 12, such as a tractor. Apparatus 10 is generally configured to facilitate positioning of one or more items in or on the ground. In one particular aspect, apparatus 10 is structured to facilitate placement of one or more items at a desired depth in the ground or soil underlying apparatus 10 as it is moved thereover during operation. Following placement of the items in the soil or ground, apparatus 10 may be further configured to cover the items. In a further aspect, apparatus 10 is configured to position one or more spherical items having a diameter in the range of about 0.25 inches to about 1.0 inches, and more particularly, but not exclusively, in the range of about 0.5 inches to about 0.75 inches, at a desired depth in the ground or soil underlying apparatus 10 as it is moved thereover during operation. In one particular form, the spherical items are capsules that include a shell wall encapsulating a pesticide composition and including a gelatin material. However, it should be appreciated that apparatus 10 may be configured to facilitate positioning of spherical items having a different diameter, or of items not having an entirely spherical configuration.

Apparatus 10 includes a toolbar 14 that provides a frame or support for positioning and supporting various components. A mounting portion 16 extends from toolbar 14 and is configured to engage with vehicle 12, which in turn may be used to move apparatus 10 and provide power to apparatus 10 from a power-take-off (PTO) or auxiliary hydraulic source, amongst other possibilities. An operator of vehicle 12 may also have access to controls for operating apparatus 10 and/or adjusting various aspects of operation of apparatus 10. In alternative non-illustrated forms, apparatus 10 may be self-driven and self-powered and any need for engagement with or control from vehicle 12 is thereby obviated.

Apparatus 10 further includes a number of containers 18 structured to hold a number of items to be released on or in the ground by apparatus 10. Each of containers 18 includes a metering unit 20 configured to selectively control release of the items from containers 18. Further details of forms of metering unit 20 will be provided below in connection with FIGS. 9-14. Metering units 20 are individually coupled to a number of application members 22 mounted to an adjustable subframe 24 of toolbar 14. Further details regarding subframe 24 and application members 22 will be provided below in connection with FIGS. 6-8. It should be understood that apparatus 10 could include a greater number of containers 18, metering units 20, and application members 22 than illustrated, or may include as few as a single container 18, metering unit 20, and application member 22. Toolbar 14 also includes a standing area 30 where an operator can, amongst other things, monitor or adjust certain aspects of operation of apparatus 10. It should also be understood that forms in which standing area 30 is omitted from apparatus 10 are possible.

Figure 2:
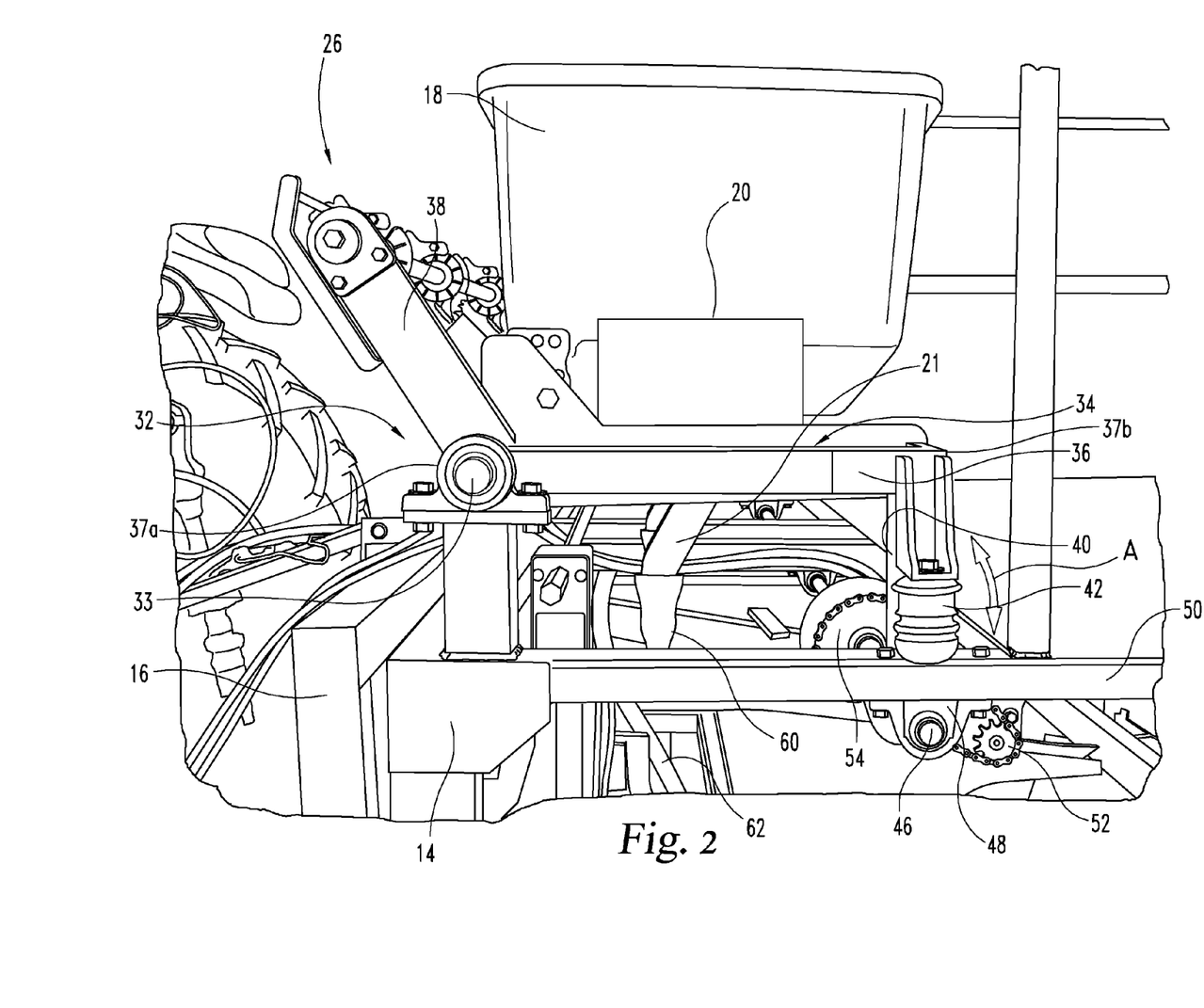
FIG. 2 is an enlarged plan view of the positioning apparatus illustrated in FIG. 1.
Figure 3:
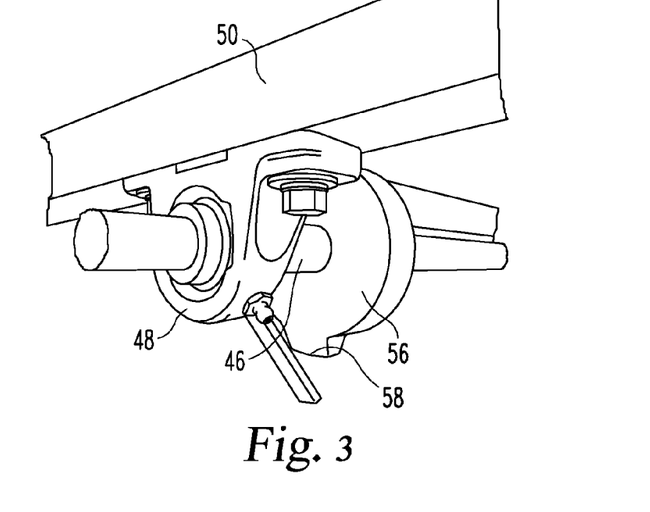
FIG. 3 is an enlarged perspective view of a portion of an actuation system of the positioning apparatus illustrated in FIG. 1.

Referring now also to FIGS. 2 and 3, apparatus 10 includes an actuation system 32 structured to selectively move containers 18 relative to toolbar 14 and, in turn, agitate any items in containers 18. More particularly, system 32 includes a platform 34 along which containers 18 are coupled and mounted. Platform 34 has a first member 36 extending between a first side 37a and a second side 37b, and a second member 38 extending obliquely from first member 36. First side 37a of first member 36 is pivotably coupled to toolbar 14 about pivot coupling 33. In this arrangement, second side 37b of platform 34 is displaceable relative to member 50 of toolbar 14 as indicated by directional arrow A. Platform 34 also includes a transverse member 40 extending from first member 36 toward member 50 of toolbar 14 and a dampening member 42 extending from first member 36. Dampening member 42 is structured to absorb and cushion impact forces that occur as second side 37b of first member 36 is moved toward and engages with member 50 of toolbar 14 during operation of actuation system 32. In one form, dampening member 42 is formed from rubber or another compressible polymer material. In another form, dampening member 42 may be in the form of a spring or spring-like member, although other variations are possible and contemplated.

Actuation system 32 further includes an elongate shaft 46 which is coupled to toolbar 14 by collar 48 and configured to rotate relative to toolbar 14. More particularly, actuation system 32 includes a first sprocket 52 interconnected to a second sprocket 54 associated with shaft 46 such that rotation of first sprocket 52 results in rotation of second sprocket 54 and of shaft 46. In one form, first sprocket 52 is driven and rotated by a hydraulic or electric motor, although other means for driving first sprocket 52 are contemplated and possible. In addition, forms in which shaft 46 is rotated directly by a hydraulic or electric motor or other means are also possible. As best seen in FIG. 3, shaft 46 includes a cam member 56 having a projecting portion 58 which intermittently engages with and bears against a portion of transverse member 40 as shaft 46 is rotated. As projecting portion 58 of cam member 56 engages with transverse member 40, second side 37b of first member 36 moves away from member 50 of toolbar 14 and results in relative displacement of platform 34 and agitation of any items in containers 18. Such agitation may eliminate or avoid, amongst other things, agglomeration of the items in containers 18 and/or clogging or obstruction of containers 18 due to agglomeration or other interaction between the items contained therein. As projecting portion 58 of cam member 56 disengages with transverse member 40 upon further rotation of shaft 46, second side 37b of first member 36 moves back toward member 50 of toolbar 14 until dampening member 42 bears thereagainst.

In the illustrated form, it should be understood that the rate of displacement of platform 34 relative to toolbar 14 and of agitation of the items in containers 18 is dependent on the rate at which shaft 46 is rotated. In one form, rotation of shaft 46 is continuous and at a constant rate during operation of apparatus 10, although forms in which rotation of shaft 46 is discontinuous and/or at non-constant rates during operation of apparatus 10 are also possible. In one particular form, rotation of shaft 46 may be associated with the speed of apparatus 10 relative to underlying ground and/or the rate at which metering units are releasing items from containers 18. For example, when relative ground speed and/or release rates of items from containers 18 are low, then shaft 46 may be rotated intermittently or at a relatively slow rate. However, as one or both of relative ground speed and release rates of items from containers 18 increases, then rotation rate of shaft 46 may be increased to resultantly increase displacement of platform 34 and agitation of the items in containers 18. Still, it should be appreciated that other techniques and parameters for operating actuation system 32 are possible.

While the illustrated form and foregoing description only provide details regarding the inclusion of a single cam member 56 on shaft 46 that engages with a single portion of platform 34, it should be understood that in non-illustrated forms actuation system 32 may include a plurality of cam members 56 that engage platform 34 at a variety of different locations. For example, in one non-illustrated form, it is contemplated that actuation system 32 may be configured such that platform 34 is intermittently engaged by separate cam members at locations adjacent to each of containers 18. It is also contemplated that, in addition to or in lieu of engagement with platform 34, each cam member of actuation system 32 may engage with and bear against a container 18 in order to agitate items stored in containers 18. Still, other arrangements for moving containers 18 relative to toolbar 14 are possible. For example, in one form, platform 34 could be positioned on a scissoring or oscillating mechanism that facilitates movement of platform 34 relative to toolbar 14. In yet another form, apparatus 10 may include one or more air shocks, ballasts, or other actuating members configured to move platform 34 relative to toolbar 14. Of course, it should also be understood that these alternative arrangements may be utilized to move containers 18 relative to platform 34 in addition to or in lieu of moving platform 34 relative to toolbar 14.

As indicated above, apparatus 10 includes a number of metering units 20 configured to selectively control release of the items from containers 18. A drive system 26 is configured to control operation of metering units 20. With more particular reference to FIGS. 4 and 5, system 26 includes an elongate shaft 66 extending between opposite ends of platform 34 and past containers 18. In the illustrated form, shaft 66 is coupled at opposite ends to second members 38 of platform 34 extending obliquely from first members 36, although it should be understood that alternative positioning of shaft 66 is contemplated. In this arrangement, shaft 66 is generally positioned above and offset from metering units 20 coupled with containers 18. System 26 also includes a drive member 64 coupled with an end of shaft 66 and configured to selectively rotate shaft 66. In the illustrated form, drive member 64 is in the form of a hydraulic motor, although other possibilities for drive member 64 are contemplated. A number of drive units 68 are spaced apart and positioned along shaft 66 and support member 71. Drive units 68 are structured to transfer rotation of shaft 66 to rotation of drive linkages 70 which are individually coupled to respective ones of metering units 20. In this arrangement, rotation of shaft 66 results in rotation of drive linkages 70, which in turn drives metering units 20 and results in operation of the same in order to release items from containers 18. It should be appreciated that other configurations for operating metering units 20 are possible and contemplated. For example, in one non-limiting form, drive units 68 and drive linkages 70 could be replaced by belts or chains that extend directly between shaft 66 and respective ones of metering units 20. In another non-limiting form, each metering unit 20 could include its own drive member directly or indirectly coupled therewith in lieu of the arrangement provided by shaft 66, drive units 68 and drive linkages 70.

Figure 4:
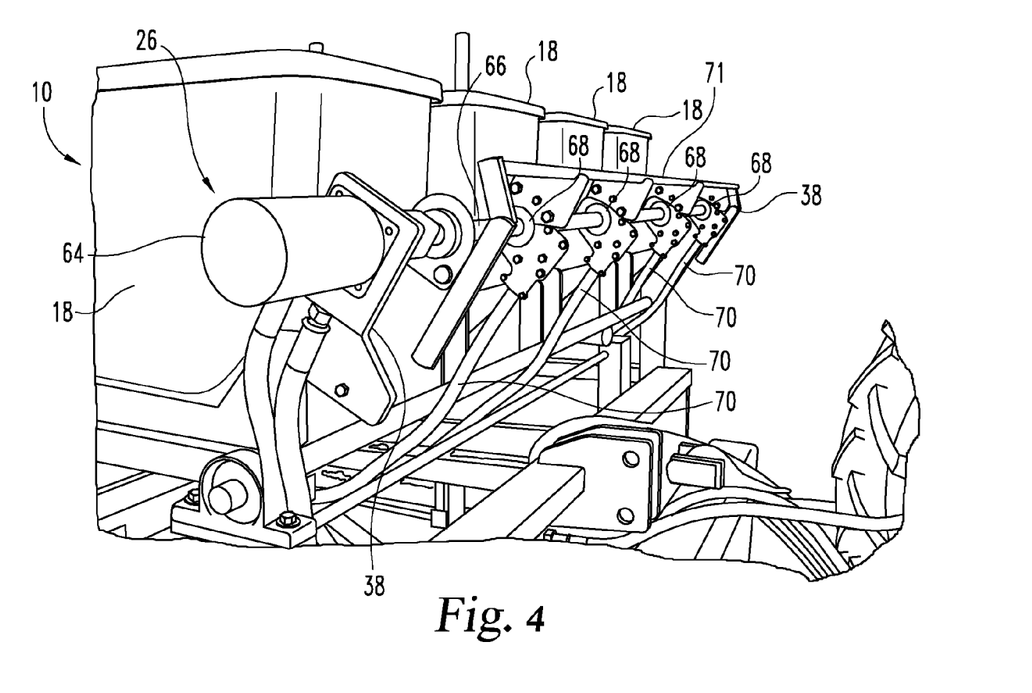
FIGS. 4 and 5 are enlarged perspective views of a drive system of the positioning apparatus illustrated in FIG. 1.
Figure 5:
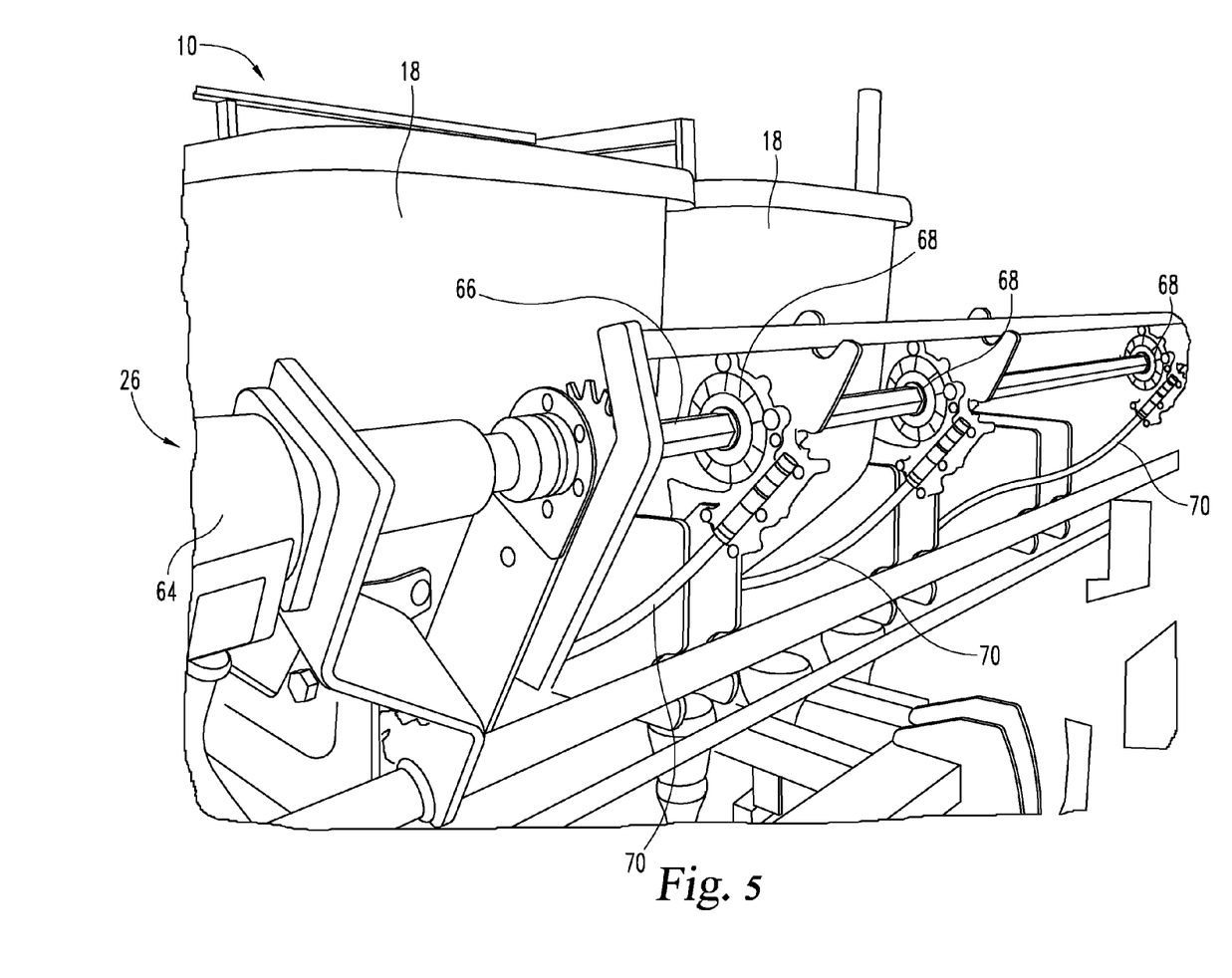

Generally speaking, the rate at which items from containers 18 will be released therefrom is dependent on the speed at which metering units 20 are driven by system 26. In one form, system 26 includes a rate controller configured to control operation of drive member 64, and rotation of shaft 66, such that the speed at which metering units 20 are operated is associated with the speed of apparatus 10 relative to underlying ground in order to maintain consistent release of items from containers 18 and spacing therebetween in the underlying soil as speeds of apparatus 10 change. For example, in one non-limiting form, as the relative speed of apparatus 10 over underlying ground increases, the rate controller reacts by increasing the operation rate of drive member 64 in order to increase the speed at which metering units 20 operate and the rate at which items will be released from containers 18. In contrast, as the relative speed of apparatus 10 over underlying ground decreases, the rate controller reacts by decreasing the operation rate of drive member 64 in order to decrease the speed at which metering units 20 operate and the rate at which items will be released from containers 18. In this arrangement, the spacing and application rate of items released from containers 18 by metering units can remain consistent regardless of the of the speed at which apparatus 10 is moved over underlying ground. Other variations in the operation of system 26 and release of items from containers 18 by metering units 20 are also possible. For example, the rate controller could upwardly or downwardly adjust the operation rate of drive member 64 in order to adjust the speed at which metering units 20 operate and the rate at which items will be released from containers 18 regardless of ground speed in order to have a higher or lower application rate of the items from containers 18 in one or more areas relative to one or more other areas. In the various different forms described above, it should be understood that the rate controller could be adjusted manually and/or be automatically responsive to changes in the relative ground speed of apparatus 10 in order to properly adjust application rates of the items from containers 18.

Figure 6:
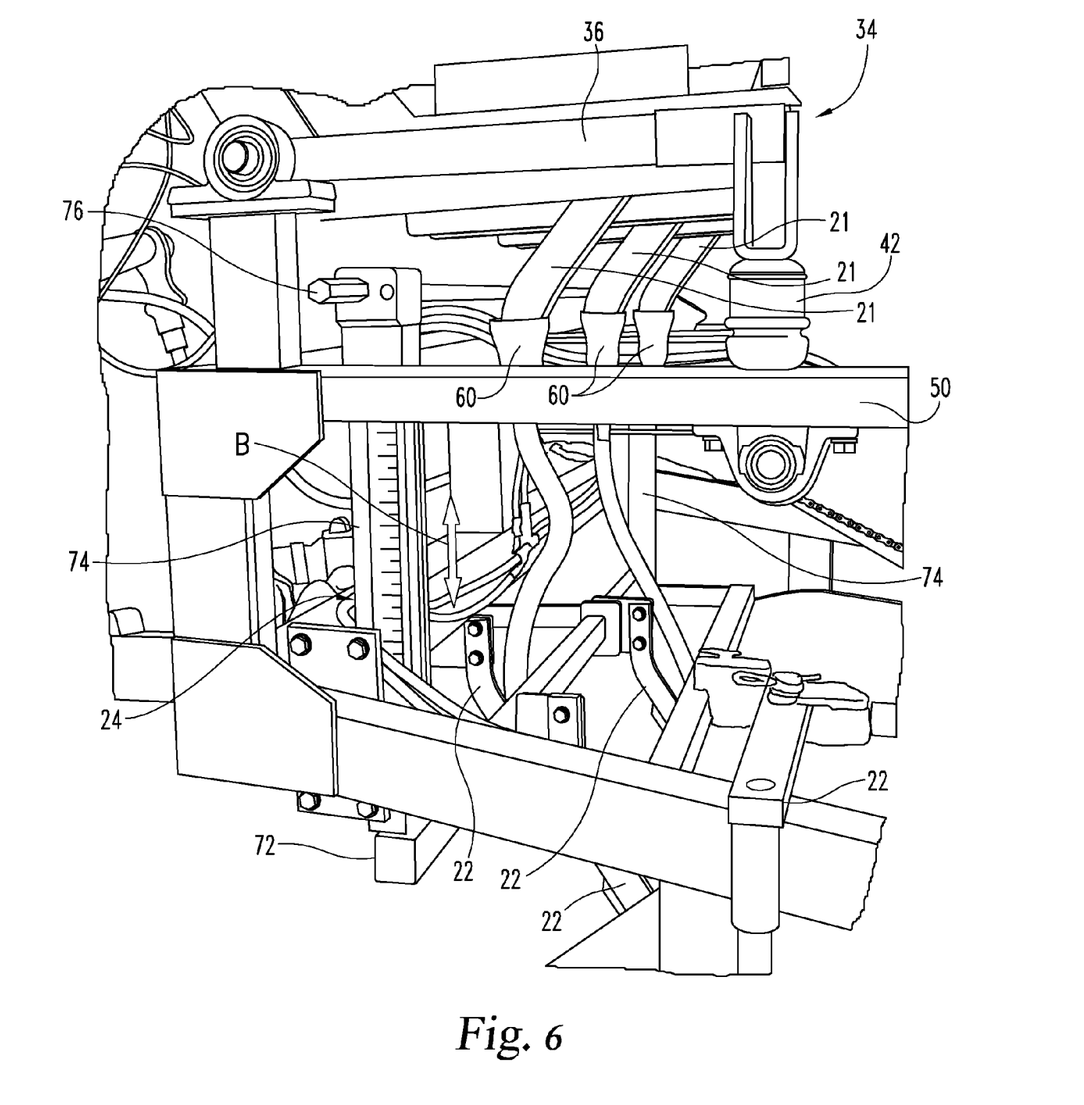
FIG. 6 is an alternative, perspective view of the positioning apparatus illustrated in FIG. 1.
Figure 8:
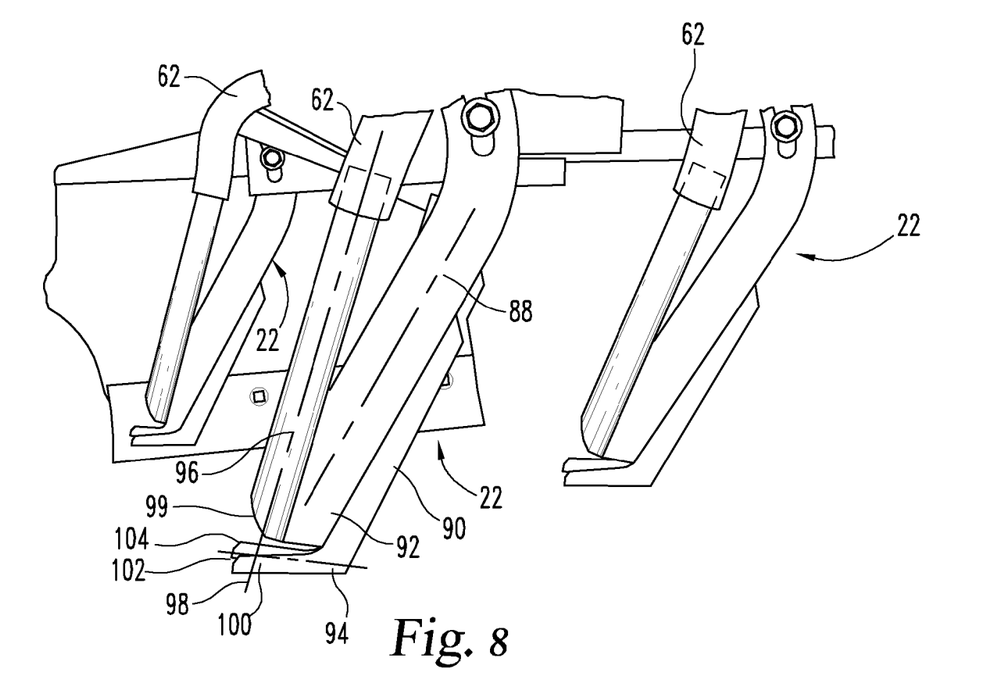
FIG. 8 is an enlarged plan view of application members of the positioning apparatus illustrated in FIG. 1.

Application members 22 are configured to position the items released from containers 18 on or in soil depending on their positioning relative to the ground underlying apparatus 10. As indicated above, application members 22 are mounted to adjustable subframe 24. As illustrated in FIGS. 6 and 8 for example, the arrangement of application members 22 is staggered relative to toolbar 14. With further reference to FIG. 6 for example, subframe 24 includes a cross member 72 extending between adjustable end members 74 and on which application members 22 are mounted. Subframe 24 also includes an adjustment mechanism 76 configured to actuate adjustable end members 74 in order to move cross member 72 relative to toolbar 14 as indicated by directional arrow B. In this arrangement, it should be understood that movement of cross member 72 relative to toolbar 14 will change the positioning of application members 22 relative to the ground underlying apparatus 10 such that items released from containers 18 may be delivered in or on soil by application members 22. For example, in one aspect, the position of cross member 72 relative to toolbar 14 can be arranged such that application members 22 are positioned above the surface of the ground underlying apparatus 10 and any items released from containers 18 are placed on top of the ground underlying apparatus 10. In another aspect, the position of cross member 72 relative to toolbar 14 can be arranged such that at least a portion of each of application members 22 is positioned below the surface of the ground underlying apparatus 10 where the application members 22 are structured to form a furrow or groove in the ground or soil as apparatus 10 is moved thereover where items released from containers 18 will be positioned. It should be further understood that the position of cross member 72 relative to toolbar 14 can be adjusted in order to change the depth of the furrows or grooves formed by application members 22 and, in turn, the depth at which items released from containers 18 will be positioned below the surface of the ground or soil.

Figure 7:
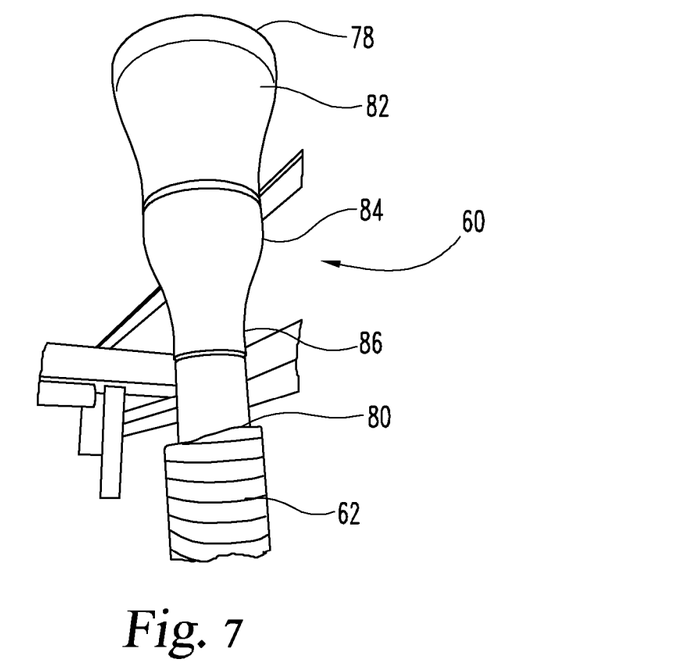
FIG. 7 is an enlarged perspective view of a guide member of the positioning apparatus illustrated in FIG. 1.

With further reference to FIG. 6 for example, each of metering units 20 includes a tubular portion 21 extending away from containers 18 toward application members 22. In the illustrated form, each of tubular portions 21 is coupled with a respective one of a plurality of guide members 60. Guide members 60 generally include a conically shaped configuration, although other possibilities are contemplated and possible. As illustrated in FIG. 7 for example, guide members 60 extend between a first end 78 to which tubular portions 21 extend, and a second end 80. Guide members 60 also include an upper portion 82 having an enlarged configuration relative to intermediate portion 84 and lower portion 86. Intermediate portion 84 has an enlarged configuration relative to lower portion 86. Guide members 60 also include a hollow interior (not shown) through which items released from containers 18 may pass. The hollow interior includes a tapered configuration that generally relates to the sizes and configuration of upper, intermediate and lower portions 82, 84, 86 of guide member 60. More particularly, the hollow interior of guide members 60 generally reduces in size from first end 78 to second end 80. In one particular form, the hollow interior of guide members 80 at upper portion 82 adjacent to first end 78 is dimensioned to have a size that is at least two times greater than a cross-sectional size of the items being released from containers 18. For example, in forms where the items released from containers 18 are spherical and include a diameter in the range of about 0.5 inches to about 0.75 inches, then the above-mentioned area of upper portion 82 would have a diameter in the range of at least 1.0 inches to at least 1.5 inches depending on the actual size of the items being released from containers 18. In the illustrated form, the diameter of the hollow interior of guide members 60 gradually decreases toward second end 80 until it reaches a size in lower portion 86 near second end 80 that is slightly larger than the cross-sectional size of the items being released from containers 18. While not previously discussed, it should be understood that the illustrated and described configuration of guide members 60 avoids or eliminates bridging of items released by metering units 20 from containers 18 and thereby facilitates delivery of the items to application members 22. Indeed, in the event items released by metering units 20 contact each other and bridge across the interior of guide members 60, then the delivery pathway to application members 22 will become blocked.

Apparatus 10 further includes a number of tubular members 62 extending between and coupling guide members 60 with application members 22. In one form, tubular members 62 may have a generally flexible configuration, although embodiments in which more rigid forms of tubular members 62 are used are also possible. As best seen in FIG. 8 for example, application members 22 include a first portion 88 that includes an end coupled to subframe 24 and generally extends along axis 90. First portion 88 includes a pointed or angled leading edge 92 which along with point 94 is configured to form a furrow or groove in soil or ground. Application members 22 also include a second portion 96 that includes an end coupled to tubular members 62 and generally extends along axis 98 which extends obliquely to axis 90. Second portion 96 includes a hollow interior configured to guide items released from containers 18 from tubular members 62 to a discharge end 99. A heel member 100 is positioned below first and second portions 88 and 96 and extends along an axis 102 that extends obliquely to both of axes 90 and 98. Heel member 100 includes a U-shaped channel portion 104 that extends below discharge end 99 of second portion 96 and is configured to guide items released from containers 18 from discharge end 99 to a location on top of underlying soil or in the furrows or grooves in the soil formed by application members 22.

Figure 9:
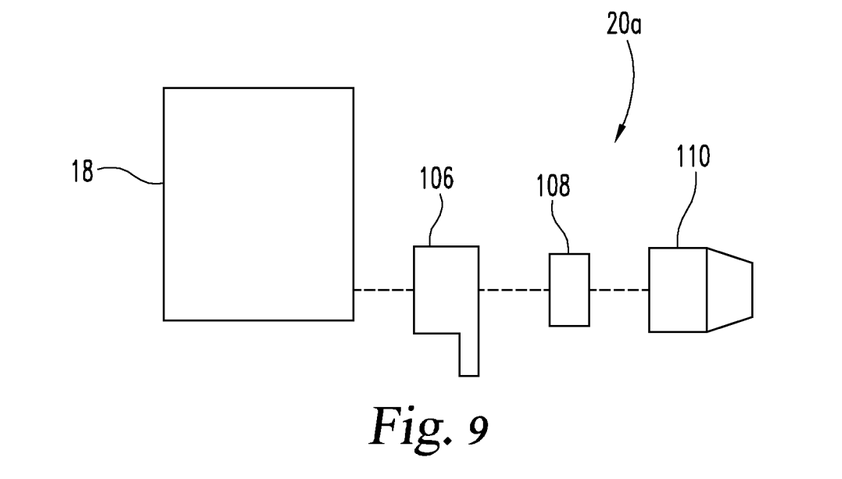
FIG. 9 is a schematic illustration of one embodiment metering unit of the positioning apparatus illustrated in FIG. 1.
Figure 10:
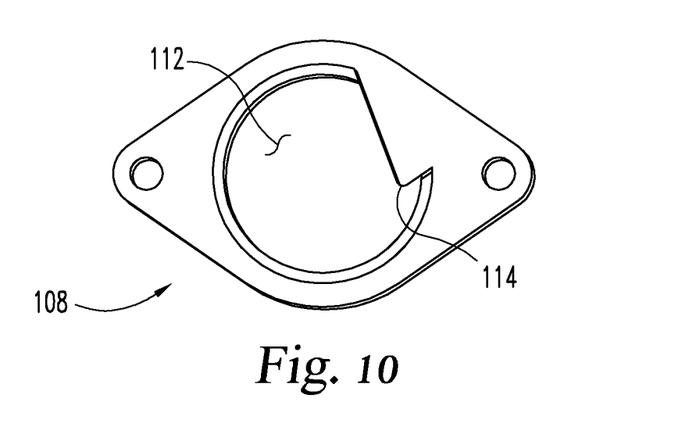
FIGS. 10 and 11 are top and side plan views, respectively, of a guide plate of the metering unit of FIG. 9.
Figure 11:
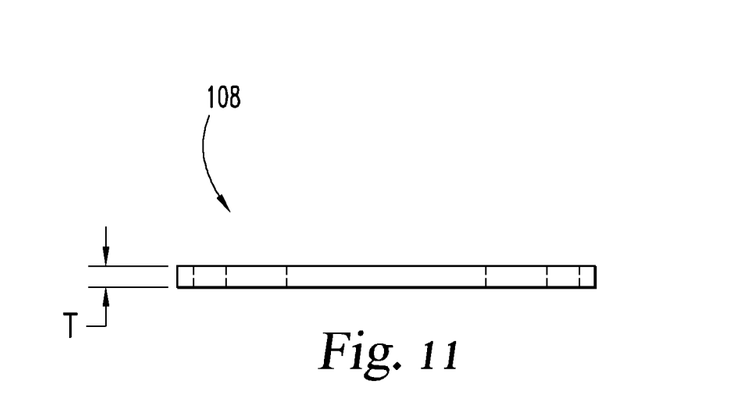

As indicated above, metering units 20 are configured to selectively control release of the items from containers 18. Various aspects of one form 20a of metering unit 20 structured for use in apparatus 10 are illustrated in FIGS. 9-11. As schematically illustrated in the assembly view of FIG. 9 for example, metering unit 20a includes a mounting member 106 which may be engaged with container 18 and from which tubular portion 21 extends. Metering unit 20a also includes a guide plate 108 and a metering cup 110. Mounting member 106 includes an aperture (not shown) extending therethrough which facilitates passage of items from container 18 through an aperture 112 (FIG. 10) of guide plate 108 into contact with metering cup 110. Metering cup 110 is driven or rotated by system 26 in order for the items to pass through aperture 112 and the rate at which items are released from containers 18 is generally dependent on the rate at which metering cup 110 is driven or rotated. As the items pass through aperture 112 and contact metering cup 110, they are rotated by metering cup 110 until they come into contact with projection 114 of guide plate 108, at which point they are released from metering cup 110 and exit metering unit 20a through tubular portion 21. While not previously discussed, it should be appreciated that operation of metering cup 110 is arranged such that the items released from containers 18 and ultimately positioned by apparatus 10 may be done so in an at least partially spatially resolved manner.

In certain aspects for example, apparatus 10 is configured to position one or more spherical items having a diameter in the range of about 0.5 inches to about 0.75 inches. In certain forms, metering unit 20a may be particularly structured for use in forms of apparatus 10 configured to position one or more spherical items having a diameter in the range of about 0.5 inches to about 0.75 inches. For example, in one form, the thickness T (FIG. 11) of guide plate 108 is dimensioned to facilitate passage of one or more items having a diameter in the range of about 0.5 inches to about 0.75 inches from containers 18 through aperture 112. In one more particular but non-limiting aspect of this form, thickness T is in the range of 0.2 inches to 0.3 inches, although other values are contemplated.

Figure 12:
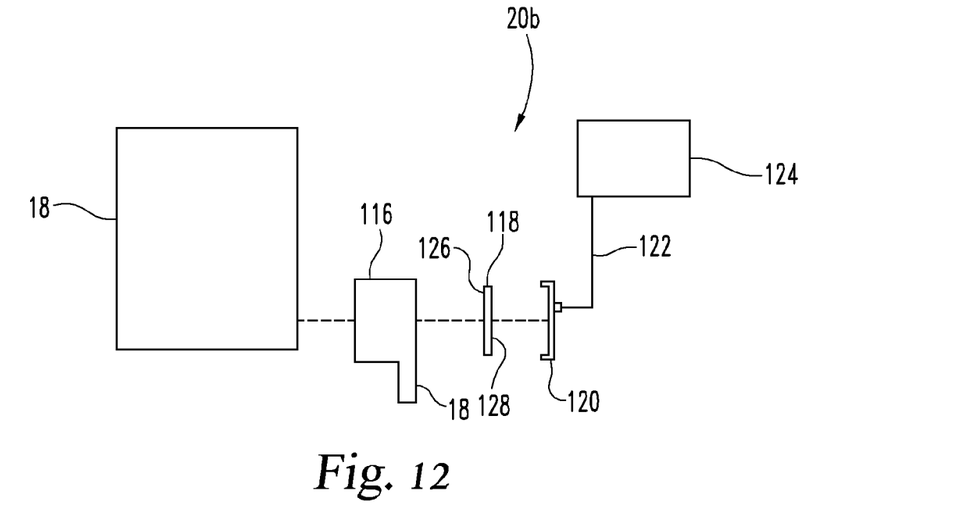
FIG. 12 is a schematic illustration of an alternative embodiment metering unit of the positioning apparatus illustrated in FIG. 1.
Figure 13:
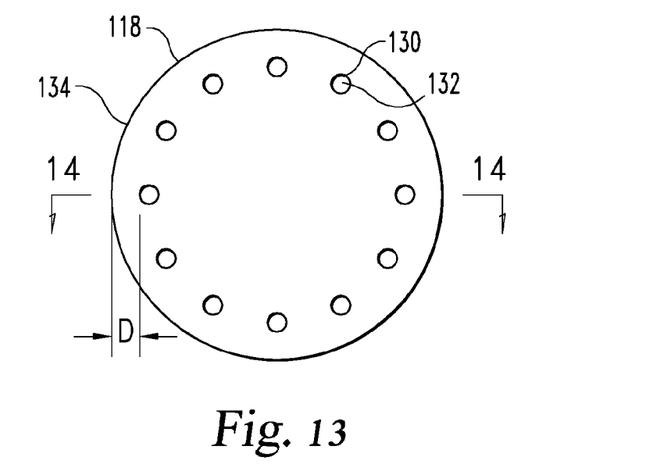
FIG. 13 is a top plan view of a metering plate of the metering unit of FIG. 12.
Figure 14:
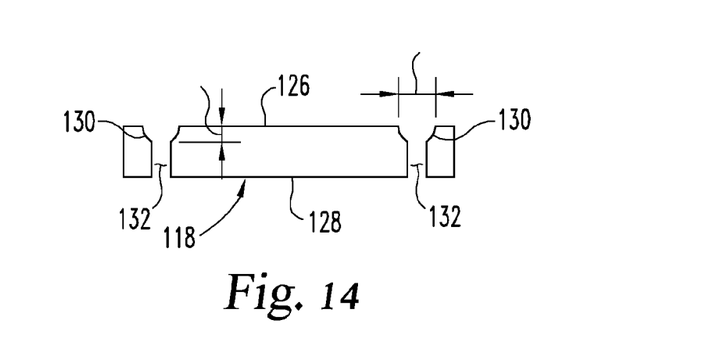
FIG. 14 is a section view of the metering plate illustrated in FIG. 13 taken along view line 14-14.

Various aspects of a vacuum metering unit 20b form of metering unit 20 structured for use in apparatus 10 are illustrated in FIGS. 12-14. As schematically illustrated in the assembly view of FIG. 12 for example, metering unit 20b includes a mounting member 116 which may be engaged with container 18 and from which tubular portion 21 extends. Metering unit 20b also includes a metering plate 118 and a cover plate 120 structured to engage with mounting member 116 and entirely or substantially enclose metering plate 118. Mounting member 116 includes an aperture (not shown) extending therethrough which facilitates passage of items from container 18 to a location adjacent to first side 126 of metering plate 118. Metering plate 118 is driven or rotated by system 26. A vacuum source 124 is coupled to cover plate 120 by pathway 122 and configured to apply a vacuum force to a portion of second side 128 of metering plate 118. Metering plate 118 also includes a plurality of spaced apart passages that extend between first and second sides 126, 128 of metering plate 118 and associated receptacles or indentations configured to receive the items from containers 18. In this arrangement, the pathways of metering plate 118 which are located in the portion of second side 128 to which the vacuum force is applied transfer the vacuum force to first side 126 of metering plate 118 which draws the items from containers 18 into the respective receptacles on first side 126 of plate 118. As this occurs, metering plate 118 is also rotated and the items drawn into the receptacles on first side 126 of plate 118 are released therefrom as the respective pathways on second side 128 are moved into an area where application of the vacuum force is not present. In one or more embodiments, a brush or other mechanism may be present to assist in release of the items from the receptacles.

Once released from metering plate 118, the items can be guided to tubular portion 21 for positioning by applications members 22 in the manner discussed above. However, it should also be understood that alternatively designed arrangements for delivering the items from metering unit 20b to their final positioning location are possible. For example, in one non-limiting form, it is contemplated that metering unit 20b is directly coupled, without guide member 60, to a location between discs or wheels that create a furrow or groove in which the items are positioned. While not previously discussed, it should be appreciated that metering unit 20b may facilitate more precise spacing or singulation of the items released from container 18 by, for example, adjusting the rate at which metering plate 118 is operated relative to the speed at which apparatus 10 is moved over underlying ground.

As indicated above, in certain aspects apparatus 10 is configured to position one or more spherical items having a diameter in the range of about 0.5 inches to about 0.75 inches. In certain forms, metering unit 20b may be particularly structured for use in forms of apparatus 10 configured to position one or more spherical items having a diameter in the range of about 0.5 inches to about 0.75 inches. For example, in one form as illustrated in FIGS. 13 and 14, metering plate 118 includes a plurality of receptacles or indentations 130 and associated pathways 132 that extend between first and second sides 126, 128 of metering plate 118. Receptacles 130 have a spherical configuration and are spaced from lateral edge 134 of metering plate at a distance D dimensioned to prevent interference between the spherical items having a diameter in the range of about 0.5 inches to about 0.75 inches and other portions of metering unit 20b when metering plate 118 is rotated or driven by system 26. In the illustrated form, receptacles 130 include a diameter $D_2$ at first surface in the range of about 0.55 inches to about 0.75 inches, although other values are contemplated. Further, receptacles 130 also extend from first surface 126 toward second surface 128 to a depth $D_3$ in the range of about 0.15 inches to about 0.25 inches, although other values are contemplated.

While not previously discussed in detail, it should be appreciated that apparatus 10 may be used to place or position, subterraneously or otherwise, a variety of different items. In one form, these items may include agricultural products such as delivery vehicles that include one or more fertilizers or pesticides or combinations of these materials. As used herein, the term "pesticide" is intended to encompass herbicides, fungicides, insecticides and bactericides. Similarly, depending on the particular form of the pesticide composition, pests that can be targeted by the disclosed delivery vehicles include insects, plant pathogens, weeds, molluscs, nematodes, and microbes. It should be appreciated however that the foregoing are merely non-limiting examples.

In one aspect, the delivery vehicle is a capsule configured to resist release of a pesticide composition before application of the capsule at a locus where pest control is desired. The capsule is further configured to degrade following application at the locus where pest control is desired to facilitate release of the pesticide composition. In certain forms, the capsule is also configured to control various aspects of the release of the pesticide composition, including for example its time and rate of release. In one particular but non-limiting form, the capsule includes a shell wall including a gelatin material and encapsulating a pesticide composition that includes a fumigant such as 1,3-dichloropropene. Further details regarding forms of this and other types of capsules that can be subterraneously placed or positioned with apparatus 10 are found in U.S. Provisional Patent Application No. 61/640,392, the contents of which are incorporated herein by reference in their entirety. In view of the foregoing, in one non-limiting embodiment apparatus 10 includes a plurality of capsules that include a pesticide composition contained in containers 18, although forms in which other types of items or capsules are stored in containers 18 are possible.

Other examples of pesticides that could be included, either singularly or in combination, in capsules that can be placed or positioned, subterraneously or otherwise, by apparatus 10 include insecticides such as antibiotic insecticides, macrocyclic lactone insecticides (for example, avermectin insecticides, milbemycin insecticides, and spinosyn insecticides), arsenical insecticides, botanical insecticides, carbamate insecticides (for example, benzofuranyl methylcarbamate insecticides, dimethylcarbamate insecticides, oxime carbamate insecticides, and phenyl methylcarbamate insecticides), diamide insecticides, desiccant insecticides, dinitrophenol insecticides, fluorine insecticides, formamidine insecticides, inorganic insecticides, insect growth regulators (for example, chitin synthesis inhibitors, juvenile hormone mimics, juvenile hormones, moulting hormone agonists, moulting hormones, moulting inhibitors, precocenes, and other unclassified insect growth regulators), nereistoxin analogue insecticides, nicotinoid insecticides (for example, nitroguanidine insecticides, nitromethylene insecticides, and pyridylmethylamine insecticides), organochlorine insecticides, organophosphorus insecticides, oxadiazine insecticides, oxadiazolone insecticides, phthalimide insecticides, pyrazole insecticides, pyrethroid insecticides, pyrimidinamine insecticides, pyrrole insecticides, tetramic acid insecticides, tetronic acid insecticides, thiazole insecticides, thiazolidine insecticides, thiourea insecticides, urea insecticides, as well as, other unclassified insecticides.

More particular examples of insecticides include, but are not limited to, labamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-endosulfan, amidithion, aminocarb, amiton, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bioresmethrin, bistrifluron, borax, boric acid, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chlorantraniliprole, chlorbicyclen, chlordane, chlordecone, chlordimeform, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyclethrin, cyclopro­thrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinoprop, dinosam, dinotefuran, diofenolan, dioxabenzofos, dioxacarb, dioxathion, disulfoton, dithicrofos, d-limonene, DNOC, doramectin, ecdysterone, emamectin, EMPC, empenthrin, endosulfan, endothion, endrin, EPN, epofenonane, eprinomectin, esfenvalerate, etaphos, ethiofencarb, ethion, ethiprole, ethoate-methyl, ethoprophos, ethyl formate, ethyl-DDD, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, fluvalinate, fonofos, formetanate, formothion, formparanate, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methylchloroform, methylene chloride, metofluthrin, metolcarb, metoxadiazone, mevinphos, mexacarbate, milbemectin, milbemycin oxime, mipafox, mirex, monocrotophos, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluthrin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulfluramid, sulfotep, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, theta-cypermethrin, thiacloprid, thiamethoxam, thicrofos, thiocarboxime, thiocyclam, thiodicarb, thiofanox, thiometon, thiosultap, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and α-ecdysone.

For more information consult "COMPENDIUM OF PESTICIDE COMMON NAMES" located at http://www.alanwood.net/pesticides/index.html. Also consult "THE PESTICIDE MANUAL" 14th Edition, edited by C D S Tomlin, copyright 2006 by British Crop Production Council.

In forms in which apparatus 10 is used to place or position, subterraneously or otherwise, a capsule that includes a pesticide, the locus to which the capsules may be applied can be any locus inhabited by a pest including, for example, areas having vegetable crops, fruit and nut trees, grape vines, grasses, and ornamental plants, just to provide a few non-limiting possibilities. Controlling pests generally means that pest populations, activity, or both, are reduced in a locus. This can come about when: pest populations are repulsed from a locus; when pests are incapacitated in or around a locus; or pests are exterminated, in whole or in part, in or around a locus. Of course a combination of these results can occur.

While the invention has been illustrated and described in detail in the drawings and foregoing description, the same is to be considered as illustrative and not restrictive in character, it being understood that only certain embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. An apparatus, comprising:
   a toolbar;
   a container;
   a metering unit configured to selectively control release of one or more items from the container;
   an application member configured to deliver the one or more items released from the container to soil; and
   an actuation system;
   wherein the container is independently displaceable by the actuation system relative to the toolbar and the application member.

2. The apparatus of claim 1, further comprising a platform including a first side pivotally coupled to the toolbar and an opposite second side displaceable relative to the toolbar.

3. The apparatus of claim 2, wherein the actuation system is configured to selectively rotate a shaft relative to the toolbar and the platform, the shaft including at least one cam member configured to intermittently bear against and move the platform relative to the toolbar upon rotation of the shaft.

4. The apparatus of claim 3, wherein the container is coupled to the platform.

5. The apparatus of claim 3, wherein the shaft is rotatably coupled to the toolbar at a location adjacent to the second side of the platform.

6. The apparatus of claim 2, further comprising one or more dampening members positioned between the second side of the platform and the toolbar.

7. The apparatus of claim 1, wherein the metering unit includes a tubular portion extending toward the application member and engaging with a guide member, the guide member extending between a first end and an opposite second end and including a hollow interior reducing in size from the first end toward the second end.

8. The apparatus of claim 7, wherein the hollow interior at the first end of the guide member is dimensioned to have a size at least two times larger than a cross-sectional size of the one or more items.

9. The apparatus of claim 8, wherein the one or more items include a plurality of gelcaps positioned in the container, the gelcaps including a diameter between about 0.5 inches and 0.75 inches.

10. The apparatus of claim 7, further comprising a flexible tubular member extending between the second end of the guide member and the application member.

11. The apparatus of claim 1, wherein the application member includes a proximal end coupled to the tool bar, a distal end positioned opposite of the proximal end, a leading edge configured to form a furrow in soil, a tubular portion configured to receive the one or more items from the metering unit, and a distal surface extending below and spaced apart from the tubular portion.

12. The apparatus of claim 11, wherein the distal surface extends obliquely to the leading edge.

13. The apparatus of claim 1, wherein the application member is coupled to a sub-frame, the sub-frame being movably adjustable relative to the toolbar.

14. The apparatus of claim 1, further comprising a drive system configured to control operation of the metering unit, the drive system including a rate controller configured to associate a release rate of the one or more items from the container with a ground speed of the apparatus.

15. The apparatus of claim 1, further comprising a drive system configured to control operation of the metering unit, wherein:
   the drive system includes an elongate shaft rotatable relative to the toolbar, a drive unit positioned along the elongate shaft, and a drive linkage extending between the drive unit and the metering unit;
   rotation of the elongate shaft actuates the drive unit and the drive linkage in order to actuate the metering unit; and
   actuation of the metering unit includes rotation of one of a metering cup and a metering plate.

16. The apparatus of claim 15, further comprising a plurality of containers, a plurality of metering units individually associated with a respective one of each of the plurality of containers, a plurality of drive units positioned along the elongate shaft, and a plurality of drive linkages individually extending between respective ones of the drive units and the metering units.

17. The apparatus of claim 1, wherein the metering unit includes a mounting member coupled to the container, a metering cup, and a guide plate positioned between the mounting member and the metering cup, the guide plate including a central aperture and a thickness dimensioned to facilitate passage of a spherical item having a diameter in the range of about 0.5 inches to about 0.75 inches from the container through the central aperture to the metering cup for release from the metering unit.

18. The apparatus of claim 17, wherein the thickness is in the range of about 0.2 inches to about 0.3 inches.

19. The apparatus of claim 1, wherein the metering unit is a vacuum metering unit and includes a metering plate, the metering plate including a first side, an opposite second side, and a plurality of substantially spherical indentations on the first side, the indentations being configured to receive and hold a spherical item having a diameter in the range of about 0.5 inches to about 0.75 inches when a vacuum force is applied to the second side.

20. The apparatus of claim 19, wherein each of the plurality of indentations is spherical and includes a diameter at a surface of the first side in the range of about 0.55 inches to about 0.8 inches.

21. The apparatus of claim 19, wherein each of the plurality of indentations extends from the first side toward the second side and includes a depth in the range of about 0.1 inches to about 0.2 inches.

22. The apparatus of claim 19, wherein each of the plurality of indentations is inwardly positioned from a lateral edge of the metering plate in an arrangement structured to prevent interference between the spherical items and an outer housing of the vacuum metering unit when the spherical items are received in the indentations.

23. An apparatus, comprising:
   a toolbar;
   a container;
   a metering unit configured to selectively control release of one or more spherical items having a diameter in the range of about 0.5 inches to about 0.75 inches from the container, the metering unit including a mounting member coupled to the container, a metering cup, and a guide plate positioned between the mounting member and the metering cup, the guide plate including a central aperture and a thickness dimensioned to facilitate passage of the one or more spherical items from the container through the central aperture to the metering cup for release from the metering unit; and
   an application member configured to deliver the one or more spherical items released from the container to soil.

24. The apparatus of claim 23, wherein the thickness is in the range of about 0.2 inches to about 0.3 inches.

25. The apparatus of claim 23, further comprising a number of capsules positioned in the container, the capsules each including a shell wall encapsulating a pesticide composition and including a gelatin material.

26. The method of claim 25, wherein the pesticide composition includes a fumigant.

27. The method of claim 26, wherein the fumigant is 1,3-dichloropropene.

28. An apparatus, comprising:
a toolbar;
a container;
a vacuum source;
a vacuum metering unit configured to selectively control release of one or more spherical items having a diameter in the range of about 0.5 inches to about 0.75 inches from the container, the vacuum metering unit being coupled with the vacuum source and including a metering plate, the metering plate including a first side, an opposite second side, and a plurality of substantially spherical indentations on the first side, the indentations being configured to receive and hold a spherical item having a diameter in the range of about 0.5 inches to about 0.75 inches when a vacuum force is applied to the second side by the vacuum source.

29. The apparatus of claim 28, wherein each of the plurality of indentations is spherical and includes a diameter at a surface of the first side in the range of about 0.55 inches to about 0.8 inches.

30. The apparatus of claim 28, wherein each of the plurality of indentations extends from the first side toward the second side and includes a depth in the range of about 0.1 inches to about 0.2 inches.

31. The apparatus of claim 28, wherein each of the plurality of indentations is inwardly positioned from a lateral edge of the metering plate in an arrangement structured to prevent interference between the spherical items and an outer housing of the vacuum metering unit when the spherical items are received in the indentations.

32. The apparatus of claim 28, further comprising an application member configured to deliver the one or more spherical items released from the container to soil.

33. The apparatus of claim 28, further comprising a number of capsules positioned in the container, the capsules each including a shell wall encapsulating a pesticide composition and including a gelatin material.

34. The method of claim 33, wherein the pesticide composition includes a fumigant.

35. The method of claim 34, wherein the fumigant is 1,3-dichloropropene.

36. A method, comprising:
positioning a number of capsules in a container of a positioning apparatus, wherein each of the capsules includes a shell wall encapsulating a pesticide composition and including a gelatin material, and the positioning apparatus includes a toolbar, a metering unit coupled to the container and configured to selectively control release of the capsules from the container and an application member coupled with the metering unit and configured to deliver the capsules released from the container to soil; and
operating the apparatus relative to adjacent soil to individually position a plurality of the capsules at separate locations in the soil.

* * * * *